(12) United States Patent
Nghiem et al.

(10) Patent No.: US 11,196,164 B2
(45) Date of Patent: Dec. 7, 2021

(54) NO-MATCHING-CIRCUIT MULTI-BAND DIVERSITY ANTENNA SYSTEM FOR MEDICAL EXTERNAL-COMMUNICATIONS

(71) Applicant: Cardiac Pacemakers, Inc., St. Paul, MN (US)

(72) Inventors: David Nghiem, Shoreview, MN (US); Peter Musto, Prior Lake, MN (US); Larry D. Canady, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/182,289

(22) Filed: Nov. 6, 2018

(65) Prior Publication Data

US 2019/0074591 A1 Mar. 7, 2019

Related U.S. Application Data

(63) Continuation of application No. 15/004,267, filed on Jan. 22, 2016, now Pat. No. 10,141,651.

(Continued)

(51) Int. Cl.
*H01Q 1/27* (2006.01)
*H01Q 9/04* (2006.01)
(Continued)

(52) U.S. Cl.
CPC ....... *H01Q 9/0407* (2013.01); *A61N 1/37229* (2013.01); *H01Q 1/38* (2013.01)

(58) Field of Classification Search
CPC .......... H01Q 1/22; H01Q 1/38; H01Q 9/0407; H01Q 9/42; H01Q 1/273; A61N 1/37229
See application file for complete search history.

(56) References Cited

U.S. PATENT DOCUMENTS

| 5,186,171 A | 2/1993 | Kuhry et al. |
| 6,930,602 B2 | 8/2005 | Dougherty et al. |

(Continued)

FOREIGN PATENT DOCUMENTS

| CN | 1922758 | 2/2007 |
| CN | 101292394 | 10/2008 |

(Continued)

OTHER PUBLICATIONS

"Communication Pursuant to Rules 161(1) and 162 EPC," for European Patent Application No. 16702868.7 dated Oct. 13, 2017 (2 pages).

(Continued)

*Primary Examiner* — Hasan Islam
(74) *Attorney, Agent, or Firm* — Pauly, DeVries Smith & Deffner LLC

(57) ABSTRACT

An antenna for electrical coupling to a wireless communication circuit includes a first conductive strip segment having a first length, a second conductive strip segment having a second length different from the first length and coupled to the first conductive strip segment at a feed point to be electrically coupled to the drive node, and a third conductive strip segment having a third length less than both the first length and the second length. A first end of the third conductive strip is coupled to the feed point and a second end is coupled to circuit ground. The first conductive strip segment provides a first specified operating frequency range at a fundamental resonance mode corresponding to the first length plus the third length, and the second conductive strip segment provides a second specified operating frequency range at a fundamental resonance mode corresponding to the second length plus the third length.

20 Claims, 8 Drawing Sheets
(1 of 8 Drawing Sheet(s) Filed in Color)

Related U.S. Application Data

(60) Provisional application No. 62/106,448, filed on Jan. 22, 2015.

(51) Int. Cl.
  *A61N 1/372* (2006.01)
  *H01Q 1/38* (2006.01)

(56) References Cited

U.S. PATENT DOCUMENTS

| | | | |
|---|---|---|---|
| 7,079,079 B2* | 7/2006 | Jo | H01Q 1/243 343/700 MS |
| 7,363,087 B2 | 4/2008 | Nghiem et al. | |
| 7,486,184 B2 | 2/2009 | Dougherty et al. | |
| 8,115,686 B2 | 2/2012 | Anguera et al. | |
| 8,352,040 B2 | 1/2013 | Von Arx et al. | |
| 8,378,910 B2 | 2/2013 | Wolf et al. | |
| 8,497,804 B2 | 7/2013 | Mateychuk et al. | |
| 10,141,651 B2 | 11/2018 | Nghiem et al. | |
| 2004/0066334 A1 | 4/2004 | Fang et al. | |
| 2004/0104849 A1 | 6/2004 | Tai et al. | |
| 2004/0125026 A1* | 7/2004 | Pathak | H01Q 1/24 343/702 |
| 2004/0212496 A1 | 10/2004 | Villaseca et al. | |
| 2005/0270245 A1 | 12/2005 | Villaseca et al. | |
| 2006/0122665 A1 | 6/2006 | Nghiem et al. | |
| 2006/0145923 A1 | 7/2006 | Autti | |
| 2006/0195162 A1 | 8/2006 | Arx et al. | |
| 2007/0030197 A1 | 2/2007 | Tsai et al. | |
| 2007/0135866 A1 | 6/2007 | Baker et al. | |
| 2007/0229358 A1 | 10/2007 | Chi et al. | |
| 2008/0288024 A1 | 11/2008 | Abrahamson et al. | |
| 2009/0102641 A1 | 4/2009 | Villaseca et al. | |
| 2009/0132008 A1 | 5/2009 | Snitting et al. | |
| 2009/0248112 A1 | 10/2009 | Mumbru et al. | |
| 2010/0060528 A1* | 3/2010 | Chiu | H01Q 1/243 343/700 MS |
| 2011/0082523 A1 | 4/2011 | Nghiem et al. | |
| 2011/0122043 A1* | 5/2011 | Ridgeway | H01Q 5/371 343/860 |
| 2012/0306700 A1 | 12/2012 | Ridgeway et al. | |
| 2013/0009839 A1 | 1/2013 | Nghiem et al. | |
| 2014/0028530 A1* | 1/2014 | Flores-Cuadras | H01Q 1/243 343/904 |
| 2014/0118194 A1 | 5/2014 | Gavilan et al. | |
| 2014/0218247 A1 | 8/2014 | Tefiku et al. | |
| 2014/0266917 A1* | 9/2014 | De Luis | H01Q 1/38 343/700 MS |
| 2016/0218433 A1 | 7/2016 | Nghiem et al. | |
| 2019/0074591 A1 | 3/2019 | Nghiem et al. | |

FOREIGN PATENT DOCUMENTS

| | | |
|---|---|---|
| CN | 101524298 | 9/2009 |
| CN | 101953022 | 1/2011 |
| CN | 103237573 | 8/2013 |
| CN | 103269750 | 8/2013 |
| CN | 103545604 | 1/2014 |
| CN | 103972646 | 8/2014 |
| CN | 107592822 | 1/2018 |
| EP | 2763240 | 8/2014 |
| EP | 3247454 | 11/2017 |
| EP | 3247454 | 7/2019 |
| JP | 2014521254 | 8/2014 |
| JP | 2018502664 | 2/2018 |
| WO | 2016118863 | 7/2016 |

OTHER PUBLICATIONS

"File History" for U.S. Appl. No. 15/004,267 downloaded Dec. 12, 2018 (240 pages).

"International Preliminary Reporton Patentability," for PCT Application No. PCT/US2016/014523 dated Aug. 3, 2017 (8 pages).

"International Search Report and Written Opinion," for PCT Application No. PCT/US2016/014523, dated Apr. 14, 2016 (13 pages).

"Response to Communication Pursuant to Rules 161(1) and 162 EPC," for European Patent Application No. 16702868.7 (our file 115.0198EPWO) filed with the EPO dated Mar. 28, 2018 (24 pages).

"Office Action," for Japanese Patent Application No. 2017-538678 dated May 21, 2019 (8 pages) with English Translation.

"First Office Action," for Chinese Patent Application No. 201680012007.2 dated Feb. 3, 2020 (17 pages).

* cited by examiner

NO-MATCHING-CIRCUIT MULTI-BAND DIVERSITY ANTENNA SYSTEM FOR MEDICAL EXTERNAL-COMMUNICATIONS

This application is a continuation of U.S. application Ser. No. 15/004,267, filed Jan. 22, 2016, which claims the benefit of U.S. Provisional Application No. 62/106,448, filed Jan. 22, 2015, the contents of which are herein incorporated by reference.

BACKGROUND

Ambulatory medical devices include implantable medical devices (IMDs) and wearable medical devices. Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and may include electrodes that are able to sense cardiac signals without being in direct contact with the patient's heart. Other examples of IMDs include implantable diagnostic devices, implantable drug delivery systems, or implantable devices with neural stimulation capability (e.g., vagus nerve stimulator, baroreflex stimulator, carotid sinus stimulator, etc.).

Some examples of wearable medical devices include wearable cardioverter defibrillators (WCDs) and wearable diagnostic devices (e.g., an ambulatory monitoring vest). WCDs can be monitoring devices that include surface electrodes. The surface electrodes may be arranged to provide one or both of monitoring to provide surface electrocardiograms (ECGs) and delivery of cardioverter and defibrillator shock therapy. A wearable medical device can also include a monitoring patch worn by the patient such as an adherable patch or a patch included with an article of clothing worn by the patient.

Wireless telemetry (e.g., low power radio frequency (RF) communication) can be used to transfer information between an ambulatory medical device and a medical device communicator. However, RF communication frequencies may be limited by governing bodies or other regulatory agencies. An RF channel available for use in one communication session may not be available for another communication session, such as when the medical device and communicator are used in different countries or regulatory jurisdictions.

OVERVIEW

As explained above, manufacturers of medical devices continue to improve and add functionality to the devices, which may result in more programmable features. One example described herein provides multi-band radio communication for the devices so that programmability can be provided in a variety of locations.

An apparatus example includes an antenna for electrical coupling to a drive node of a wireless communication circuit of an external medical communicator. The antenna comprises a first conductive strip segment having a first length; a second conductive strip segment having a second length different from the first length and coupled to the first conductive strip segment at a feed point to be electrically coupled to the drive node; and a third conductive strip segment having a third length less than both the first length and the second length. A first end of the third conductive strip is coupled to the feed point and a second end coupled to circuit ground. The first conductive strip segment is configured to provide a first specified operating frequency range at or near a fundamental resonance mode corresponding to the first length plus the third length, and the second conductive strip segment is configured to provide a second, higher, specified operating frequency range at or near a fundamental resonance mode corresponding to the second length plus the third length.

In addition or alternatively, the third length is a specified fraction of an overall length corresponding to the first length plus the third length, and the antenna is coupled to the drive node to transfer information without an impedance matching circuit.

In addition or alternatively, the first conductive strip segment includes a plurality of turns so that a first section of the first conductive strip segment is arranged to be substantially parallel to the second conductive strip segment on a first side and a second section of the first conductive strip segment is arranged to be substantially parallel to the second conductive strip segment on a second side. In addition or alternatively, the second conductive strip segment and the first conductive strip segment are arranged on a flexible circuit substrate, wherein the flexible circuit substrate, the second conductive strip segment, and the sections of the first conductive strip segment parallel to the second conductive strip segment include a bend of substantially a right angle. In addition or alternatively, a first portion of the first conductive strip segment and a first portion of the second conductive strip segment are coplanar in a first plane, and a second portions of the first conductive strip segment and a second portion of the second conductive strip segment are coplanar in a second plane, wherein the second plane is substantially orthogonal to the first plane.

In addition or alternatively, the first conductive strip segment and the third conductive strip segment are sized for communication in a medical implant communication service (MICS) extended frequency band, and the second conductive strip segment and the third conductive strip segment are sized for communication in a short range device (SRD) or a North American industrial, scientific, and medical (ISM) frequency band.

In addition or alternatively, a fourth conductive strip segment is included for electrical coupling to a second drive node of the wireless communication circuit, wherein the fourth conductive strip segment has a fourth length less than the first length or the second length and is coupled to the third conductive strip segment at a second feed point to the second drive node, and wherein the fourth conductive strip segment is configured to provide a third specified operating frequency range at or near a resonance mode of a higher order than a fundamental resonance mode corresponding to the fourth length plus the third length. In addition or alternatively, the fourth conductive strip segment and the third conductive strip segment are sized for communication in a Wi-Fi frequency band.

In addition or alternatively, the first conductive strip segment and the second conductive strip segment comprise monopole-like antennas.

This section is intended to provide a brief overview of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

Medical devices and associated medical device communicators often use a variety of different wireless radio frequency communication frequencies and protocols to communicate, such as where different countries or regulatory authorities dictate the frequencies or bands that may be used for such communication. Building medical devices that are able to communicate using different frequencies and protocols typically involves use of multiple antennas, as antennas are typically configured to have specific lengths based on the fundamental wavelength or frequency of the RF signal used. Further, varying the configuration or geometry of antennas can cause the antennas to have a varying characteristic impedances, such that a system having multiple antennas often requires impedance matching circuitry to efficiently drive at least some of the antennas. Some examples presented herein therefore employ an antenna configuration having multiple antenna segments that are driven from a single feed point, such that various antenna segments are combined to form effective antennas of various lengths corresponding to desired frequencies, and such that impedance matching circuitry is not required.

Figure 1:
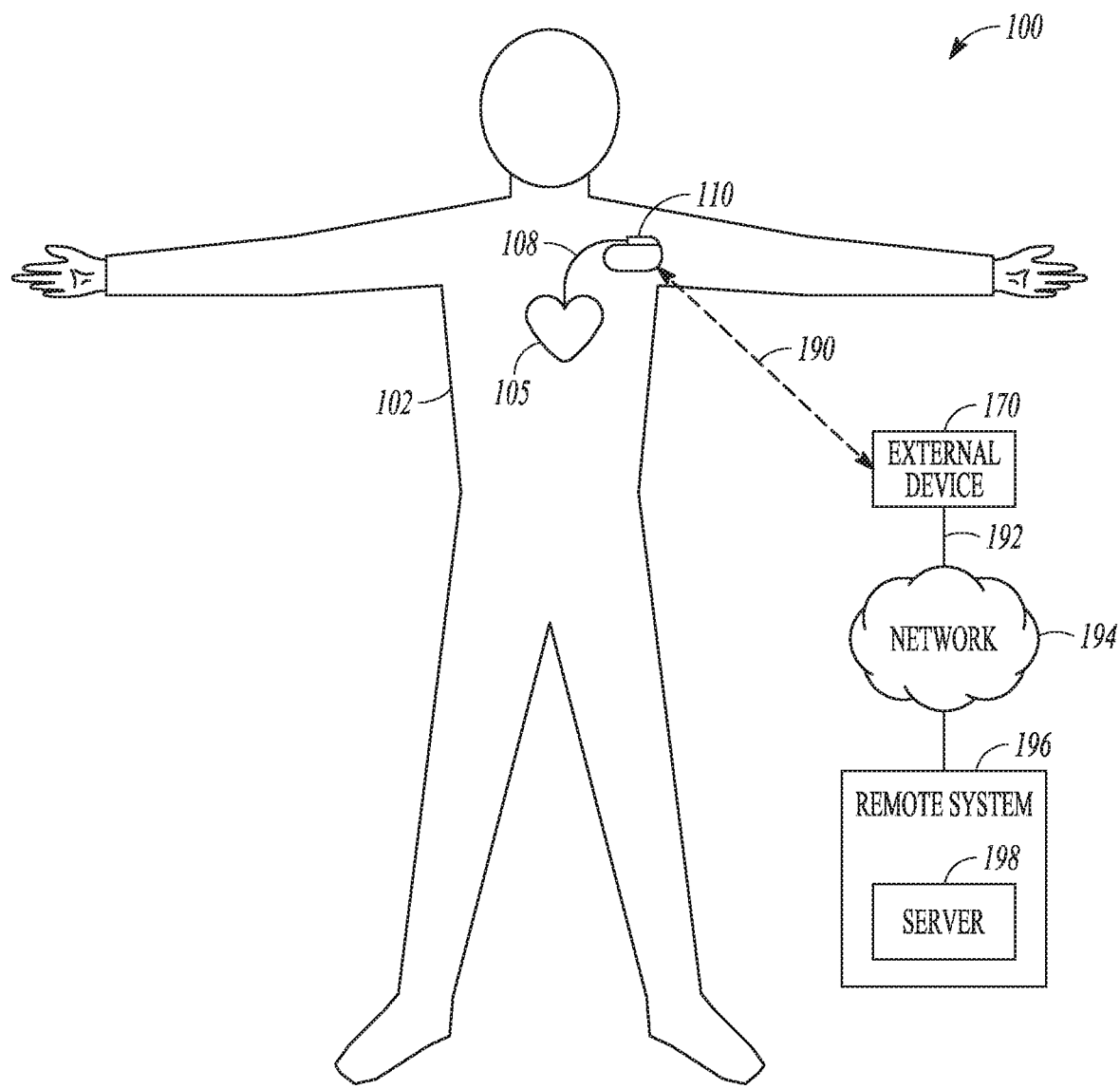
FIG. 1 is an illustration of portions of an example of a medical device system that includes an ambulatory medical device.

FIG. 1 is an illustration of portions of an example of a medical device system that includes an ambulatory medical device that is an IMD 110 that provides a therapy to a patient 102. In the example shown, the IMD 110 includes cardiac lead 108 to provide electrical therapy to the patient's heart 105. The system 100 typically includes an external medical device 170 (e.g., an external medical communicator) that can communicate wireless signals 190 with the IMD 110, such as by using RF or other telemetry signals. The external medical device 170 may communicate with a remote system 196 via a network 194. The network 194 can be a communication network such as a phone network or a computer network (e.g., the internet). In some examples, the external device includes a repeater and communicates via the network using a link 192 that may be wired or wireless. In some examples, the remote system 196 provides patient management functions and may include one or more servers 198 to perform the functions.

Figure 2:
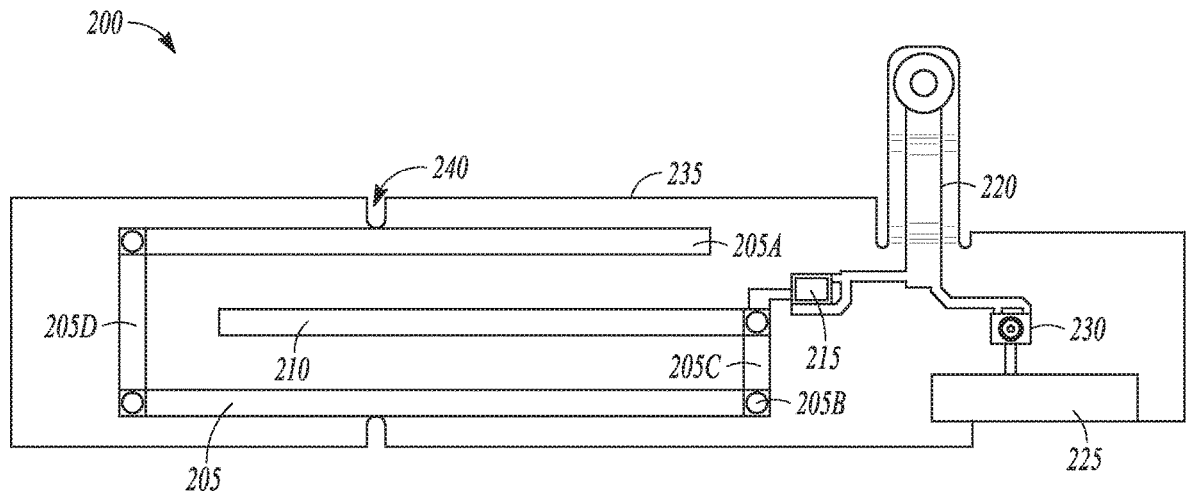
FIG. 2 illustrates an example of an antenna for inclusion in an external medical device.

FIG. 2 illustrates an example of an antenna for inclusion in an external medical device such as an external medical communicator. The external medical communicator may be a programmer for the ambulatory medical device. To transfer information, the antenna is electrically coupled to a drive node of a wireless communication circuit of the external medical communicator.

Figure 3:
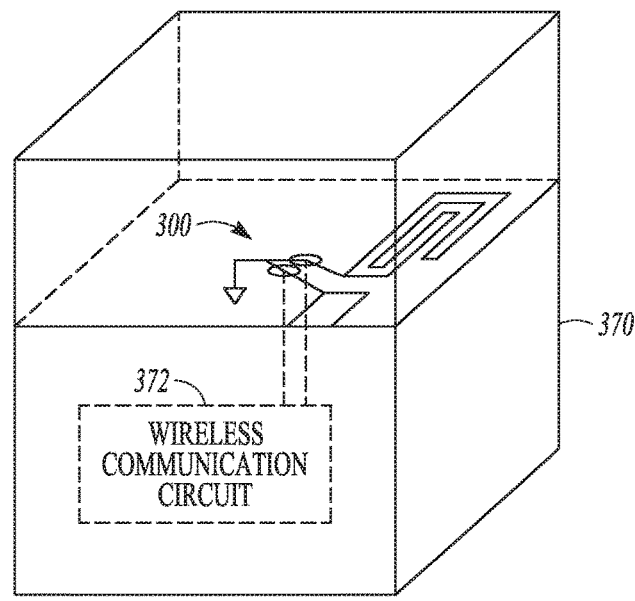
FIG. 3 illustrates portions of an example of an electronic assembly for an external medical device.

FIG. 3 illustrates portions of an example of an electronic assembly for an external medical device 370. The electronic assembly includes a wireless communication circuit 372 (e.g., a wireless transceiver) and an antenna 300 coupled to a drive node of the wireless communication circuit 372.

Returning to FIG. 2, the antenna 200 includes a first conductive strip segment 205 having a first length and a second conductive strip segment 210 having a second length different from the first length. The second conductive strip segment 210 is coupled to the first conductive strip segment 205 at a feed point 215 that is to be electrically coupled to the drive node of the wireless communication circuit. In some variations, a coaxial cable connector is arranged at the feed point 215 for connection to the drive node.

The antenna 200 also includes a third conductive strip segment 220 having a third length less than both the first length of the first conductive strip segment and the second length of the second conductive strip segment. The first end of the third conductive strip is coupled to the feed point 215 and the second end is coupled to circuit ground or a ground point.

The first conductive strip segment 205 is configured (e.g., by size and shape) to provide a first specified operating frequency range at or near a fundamental resonance mode corresponding to the first length plus the third length of the third conductive strip segment 220. In certain examples, the first conductive strip segment 205 and the third conductive strip segment 220 are sized for communication in a medical implant communication service (MICS) extended frequency band (e.g., a specified operating frequency in the range of band of 401-406 MHz).

The second conductive strip segment 210 is configured to provide a second, higher, specified operating frequency range at or near a fundamental resonance mode corresponding to the second length plus the third length of the third conductive strip segment 220. In certain examples, the second conductive strip segment 210 and the third conductive strip segment 220 are sized for communication in a short range device (SRD) frequency band (e.g., a specified operating frequency in the European (EU) SRD bands of 433-435 MHz and 862-870 MHz (such as 869.85 MHz), and the Japanese SRD bands within the range of 420 MHz-450 MHz). In certain examples, the second conductive strip segment 210 and the third conductive strip segment 220 are sized for communication in the North American industrial, scientific, and medical (ISM) frequency band (e.g., a specified operating frequency in the range of 902-928 MHz (such as 916.50 MHz)).

Figure 4:
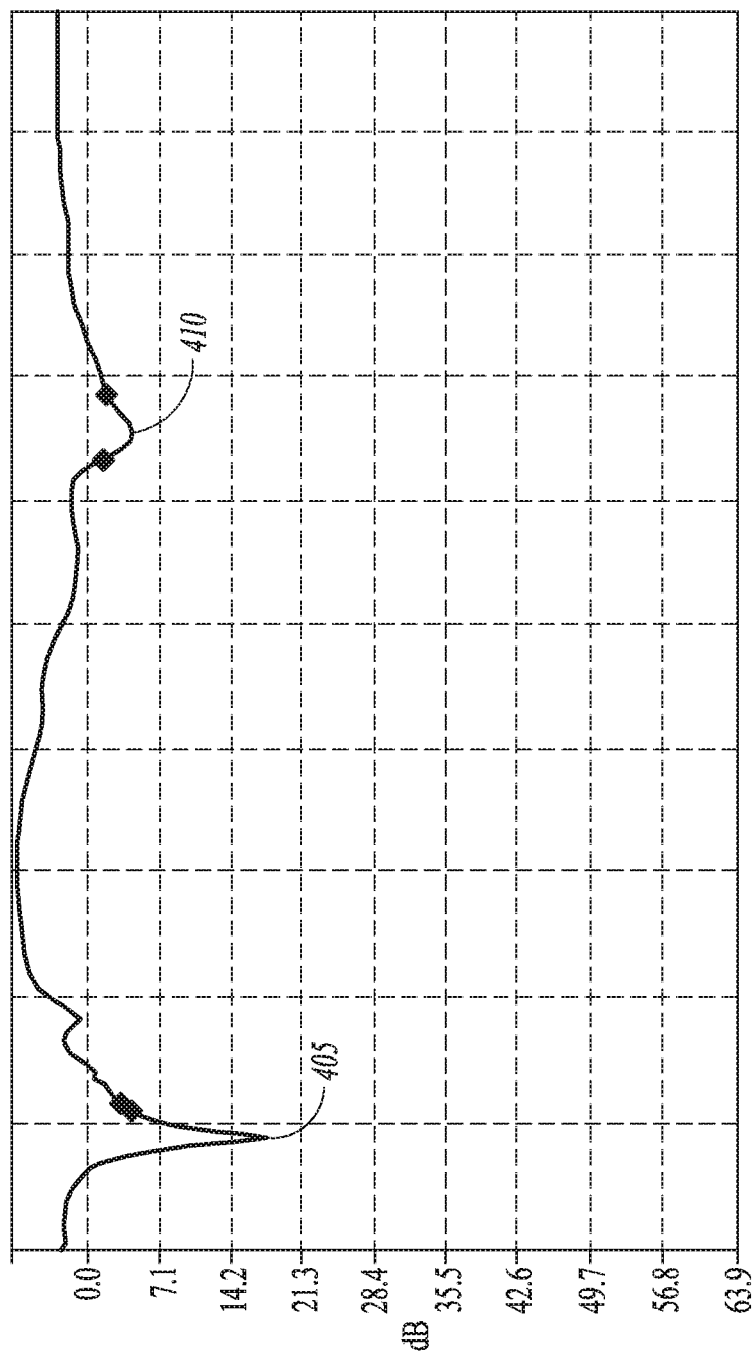
FIG. 4 shows a graph of antenna return-loss response for an example antenna.

The discussion above shows that the antenna 200 provides multi-band diversity. FIG. 4 shows a graph of antenna return-loss response versus frequency for an example antenna. The graph shows a first mode 405 of operation and a second mode 410 of operation.

Typically, an antenna feed point is arranged at an end of a conductive strip, such as at a symmetrical point where two conductive segments of a dipole antenna are joined. The arrangement of the feed point 215 in FIG. 2 offsets the feed point making the antenna asymmetric. As discussed further herein, the offset arrangement described was found to help minimize metal frame effects on the antenna.

Figure 9A:
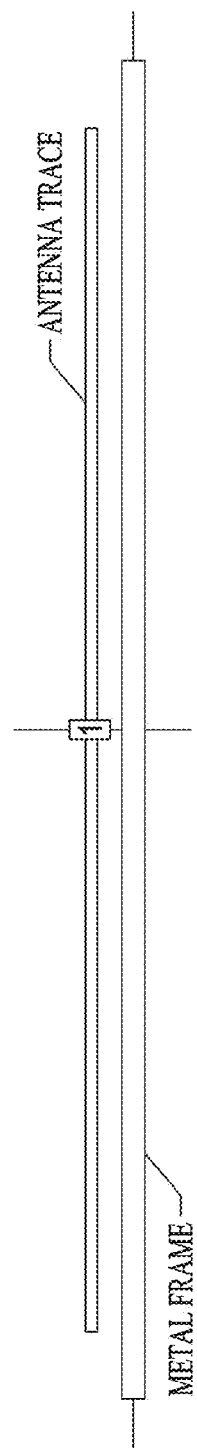
FIGS. 9A and 9B illustrate examples of antennas and metal frames.
Figure 9B:
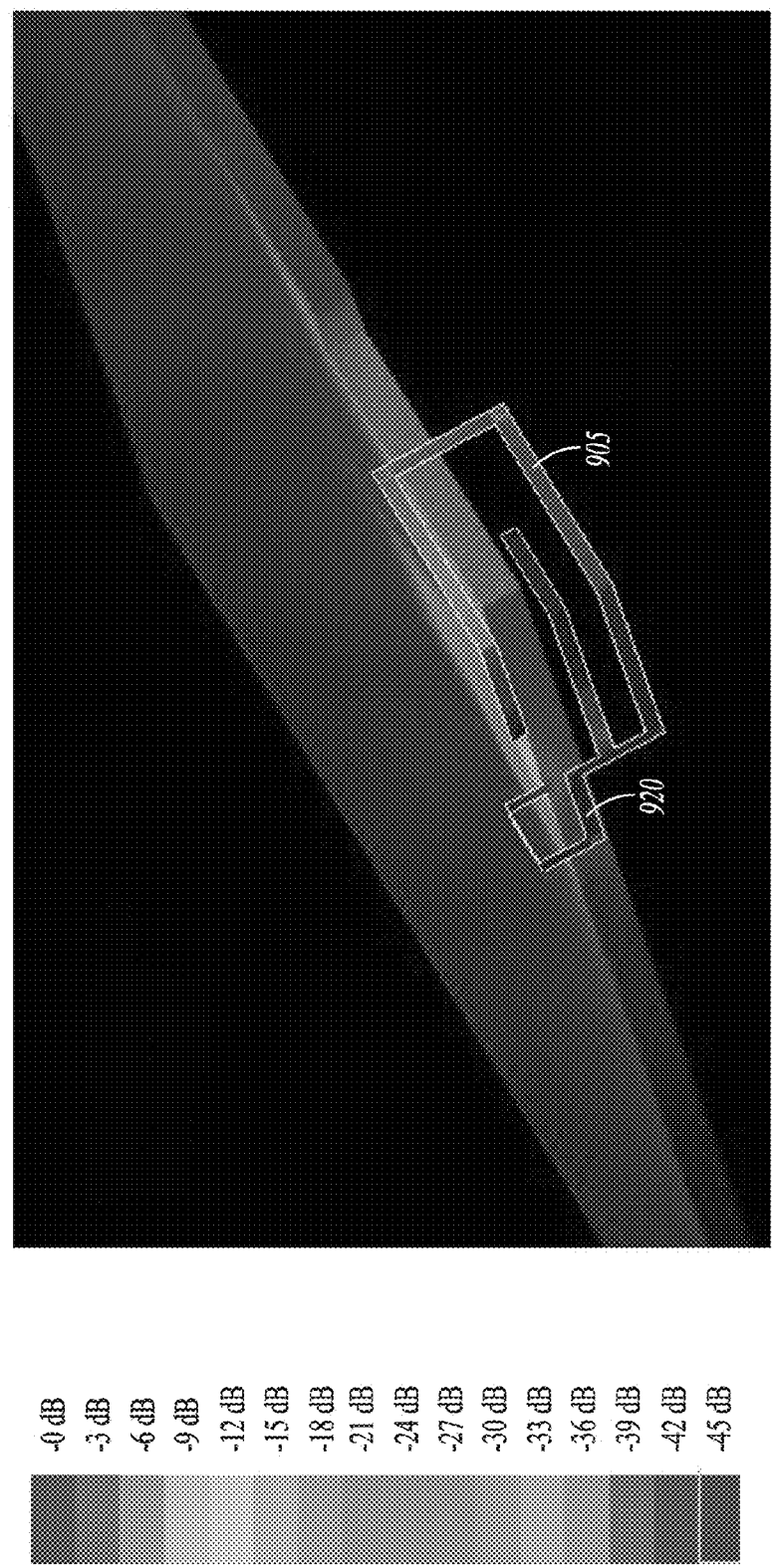

FIGS. 9A and 9B illustrate examples of antennas and metal frames, such as a metal frame included in an assembly for an external medical communicator (e.g., 170 in FIG. 1). FIG. 9A is an illustration of a dipole antenna with two equal antenna elements joined at a symmetrical feed point (indicated by the "1" in FIG. 9A). The antenna is parallel to the metal frame and extends over the metal frame. This arrangement results in the incident energy causing strong surface currents in the metal frame and less current in the antenna.

FIG. 9B illustrates an antenna having a shape such as the example antenna of FIG. 2. The Figure also shows a large planar metal frame, and the distribution of surface current both in the antenna and in the metal frame near the antenna for an operating frequency of 401 MHz. The legend to the left of the graph shows the relative values of the surface current in the Figure relative to a maximum current level of 0 decibels, such that red and yellow colors show higher current densities while green and blue colors show lower current densities. The example of FIG. 9B shows that most of the energy used to drive the antenna results in surface current in the antenna, and relatively little energy is radiated into the metal frame, and more particularly, that most of the energy is located in the first conductive strip segment 905 and the third conductive strip segment 920. This current distribution therefore shows that a significant portion of energy used to drive the antenna is radiated from the first and third conductive strip segments 905, 920 of the antenna, which effectively form a center-driven dipole-type antenna at this frequency, with relatively little energy being absorbed by the metal frame or being radiated by the second conductive strip segment (210 in FIG. 2). FIG. 9B therefore shows that the structure of the antenna minimizes the metal frame effects, and provides an effective dipole antenna at the specified frequency.

Figure 5:
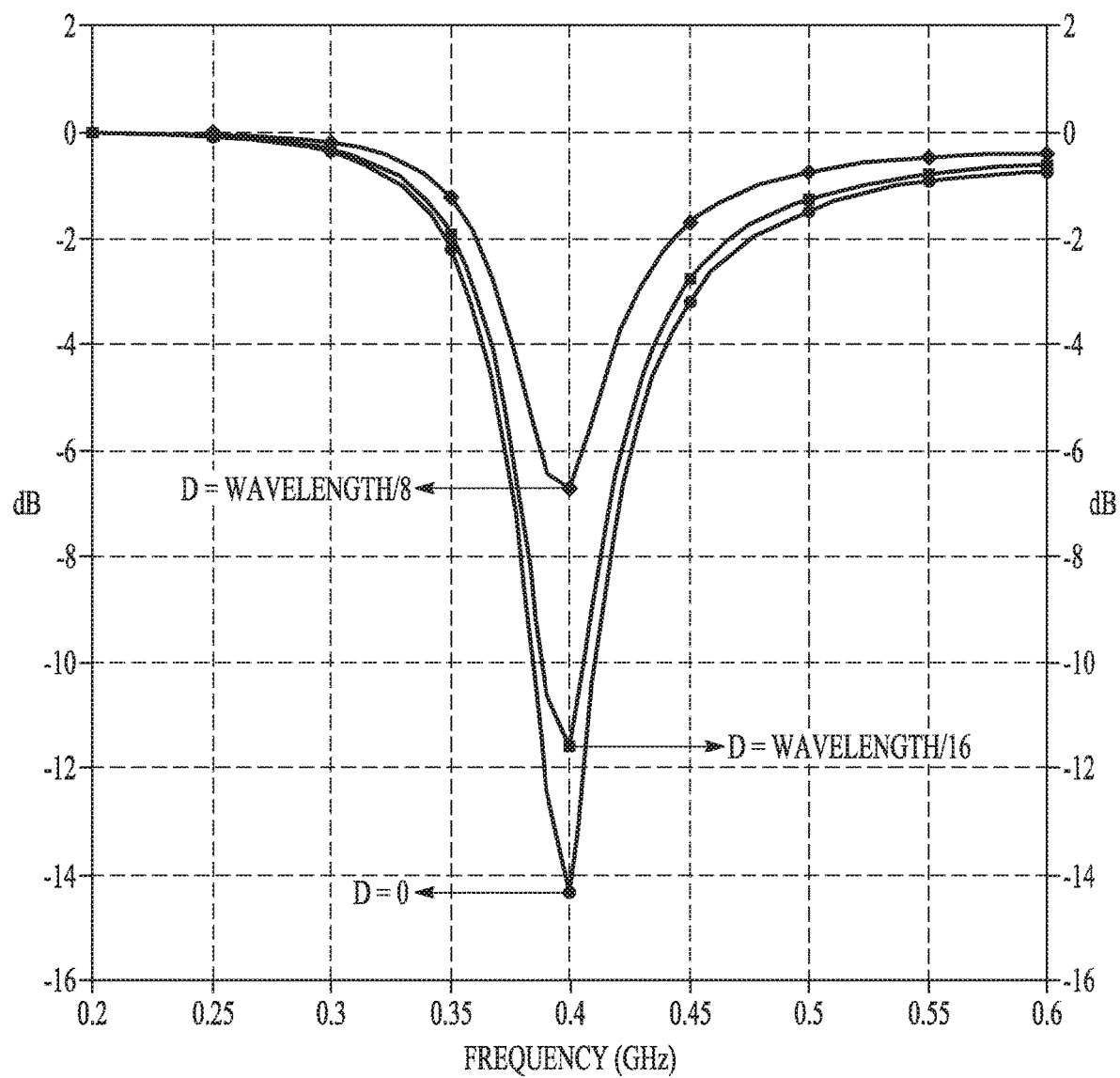
FIG. 5 shows a graph of return loss for an example antenna.

Returning to FIG. 2, proper sizing the length of the third consecutive strip segment 220 can remove the need for a separate circuit for impedance matching of the antenna 200 (e.g., at the feed point 215). For example, FIG. 5 shows a graph of antenna return-loss versus frequency for an example antenna configured for operation in the MICS band. The graph shows the response for three different lengths of offset D, where D is the offset point or feed point corresponding to the length of the third conductive strip segment 220. The graph shows that for different lengths of D=0, D=$\lambda$/16, and D=$\lambda$/8, the D=0 example has the best response, but the response for the length D=$\lambda$/8 may still be useful depending upon the application. Thus, in some examples the antenna 200 can be coupled to the drive node of the wireless communication circuit to transfer information without an impedance matching circuit. However, increasing the length further than what is shown in FIG. 5 (e.g., to D=$\lambda$/4) may result in diminished performance without the use of an impedance matching circuit.

In some examples, the third length (the length of the third conductive strip segment 220) is a specified fraction of the first length (of the first conductive strip segment 205) plus the third length. As an illustrative example, if the overall length corresponding to the first length plus the third length is selected for a resonance mode according to one fourth of a wavelength or $\lambda$/4, the length of the third consecutive strip segment 220 can be selected to be $\lambda$/8 to provide good impedance matching.

In some examples, the antenna 200 includes a fourth conductive strip segment 225. The fourth conductive strip segment 225 can be coupled to a second drive node of the wireless communication circuit, such as at second feed point 230. The fourth conductive strip segment 225 has a fourth length less than the first length (of the first conductive strip segment 205) or the second length (of the second conductive strip segment 210). The fourth conductive strip segment 225 is coupled to the third conductive strip segment 220 at the second feed point 230. The fourth conductive strip segment 225 is configured to provide a third specified operating frequency range at or near a resonance mode of a higher order than a fundamental resonance mode corresponding to the fourth length plus the third length (e.g., the second higher order from the fundamental order). In certain examples, the fourth conductive strip segment 225 and the third conductive strip segment 220 are sized for communication in a Wi-Fi frequency band (e.g., an operating frequency of 2.4 gigahertz (GHz) or 5.8 GHz).

The conductive strip segments can include one or more turns. In the example of FIG. 2, the first conductive strip segment 205 includes multiple turns. A first section 205A of the first conductive strip segment is arranged to be substantially parallel to the second conductive strip segment on a first side and a second section 205B of the first conductive strip segment is arranged to be substantially parallel to the second conductive strip segment on a second side. The term substantially parallel can mean that the portions will not likely intersect if the segments were to be extended by the second length. The turns in the first conductive strip segment results in sections 205C and 205D of the first conductive strip segment being perpendicular to sections 205A and 205B. The perpendicular sections can provide polarization diversity of radiation from and to the antenna 200.

FIG. 2 also shows a flexible circuit substrate 235. The first conductive strip segment 205 and the second conductive strip segment 210 are arranged on the flexible circuit substrate 235. The flexible circuit substrate 235 includes a notch 240 to accommodate folding. In some examples, the flexible circuit substrate, the second conductive strip segment, and the sections of the first conductive strip segment parallel to the second conductive strip segment include a bend of substantially a right angle (e.g., a bend of about 90 degrees or a bend in the range of 75-105 degrees).

Figure 10:
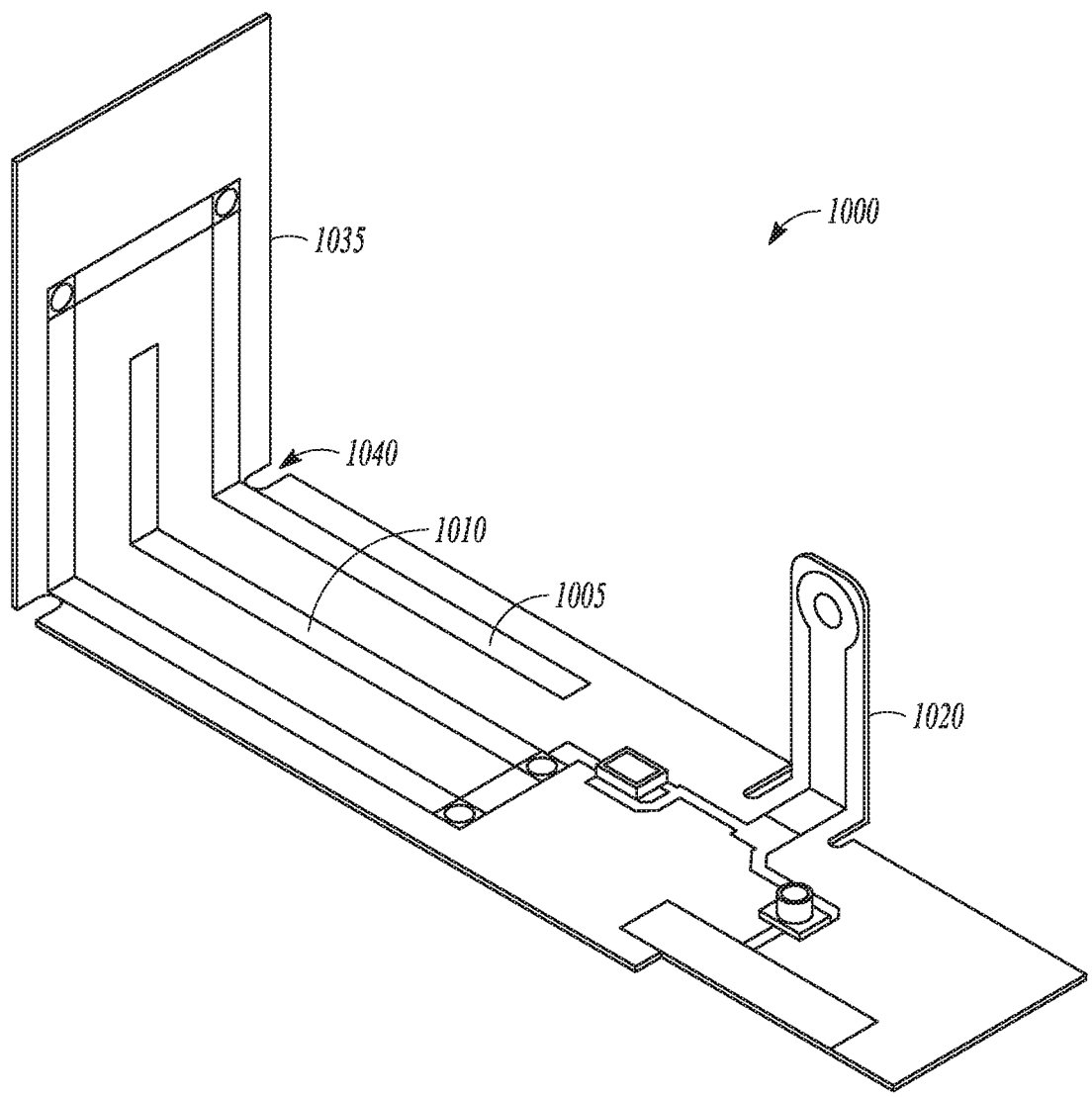
FIG. 10 shows another example of an antenna.

FIG. 10 shows an example of an antenna 1000 with a bend in the flexible substrate 1035. The bend to the antenna can further provide polarization diversity of radiation from and to the antenna. In some examples, the portion of the first conductive strip segment 1005 to the right of the notch 1040 and the portion of the second conductive strip segment 1010 to the right of the notch 1040 are coplanar in a first plane. After bending, the portion of the first conductive strip segment 1005 to the left of the notch 1040 and the portion of the second conductive strip segment 1010 to the left of the notch are coplanar in a second plane. If the bend is substantially a right angle, the second plane is substantially orthogonal to the first plane. This bending provides a three-dimensional antenna with improved direction diversity by the antenna being able to transmit and receive radiation polarized in multiple orientations. The example of FIG. 10 also shows a bend to third conductive strip segment 1020. This also adds direction diversity to the antenna.

Figure 6:
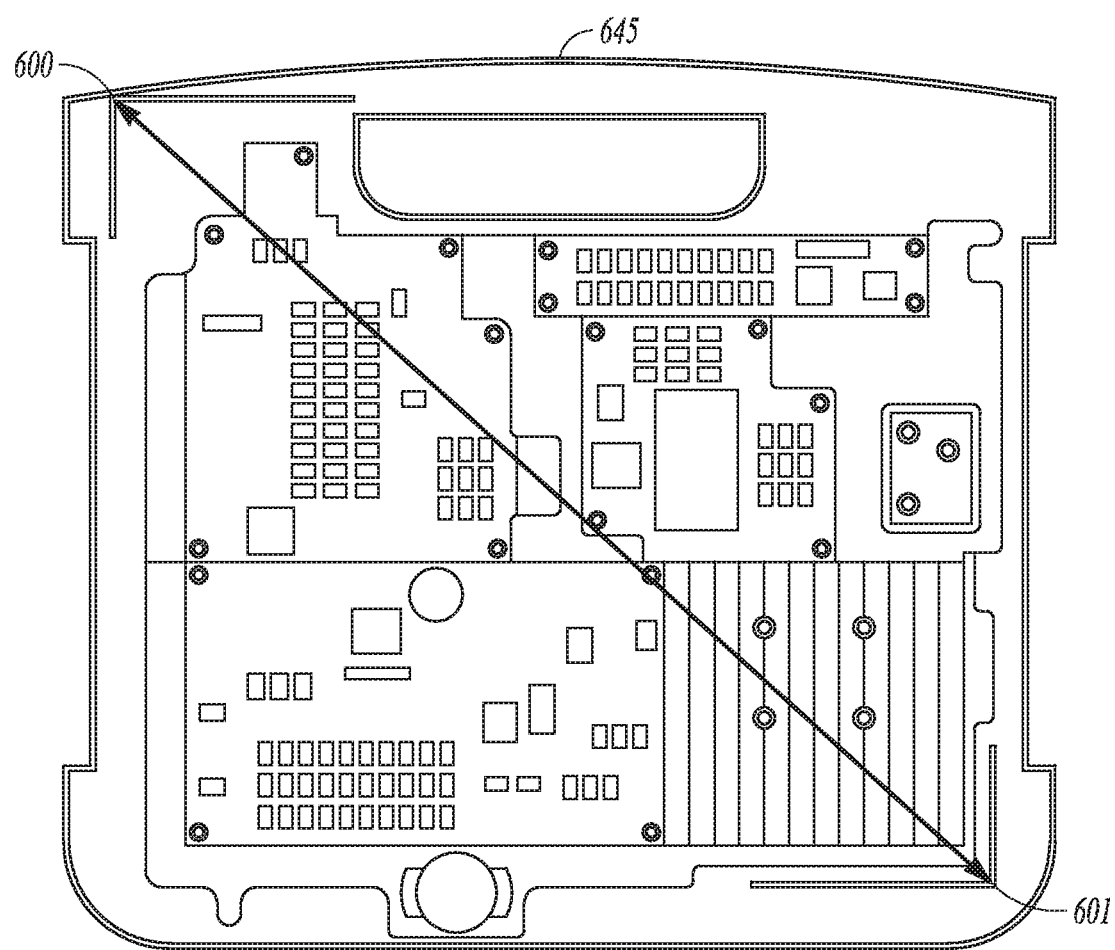
FIG. 6 shows an example an external medical communicator assembly.

FIG. 6 shows an example of an external medical communicator assembly 645. The external medical communicator assembly 645 includes two antennas; a first antenna 600 at the upper left corner and a second antenna 601 at the lower right corner. Both antennas include a bend of substantially a right angle to accommodate the placement shown and to provide polarization diversity. The placement shown also maximizes spatial diversity of the antennas by the placement in the opposite corners. In some variations, the external medical communicator assembly 645 includes four antennas, one placed at each corner of the assembly. In some variations, the external medical communicator assembly 645 includes three antennas. In some variations, the external medical communicator assembly 645 includes three antennas with each one placed at a different corner of the assembly. The example of FIG. 9B and FIG. 10 show one or more bends in the antenna in the conductive strip segment 920 and 1020, respectively. Bends in the third conductive strip segment, bends in the first and second conductive strip segments and the perpendicular sections of the first conductive strip segment reduce the polarization of the radiation from and to the antenna, providing for more reliable communication in different spatial configurations.

Figure 7:
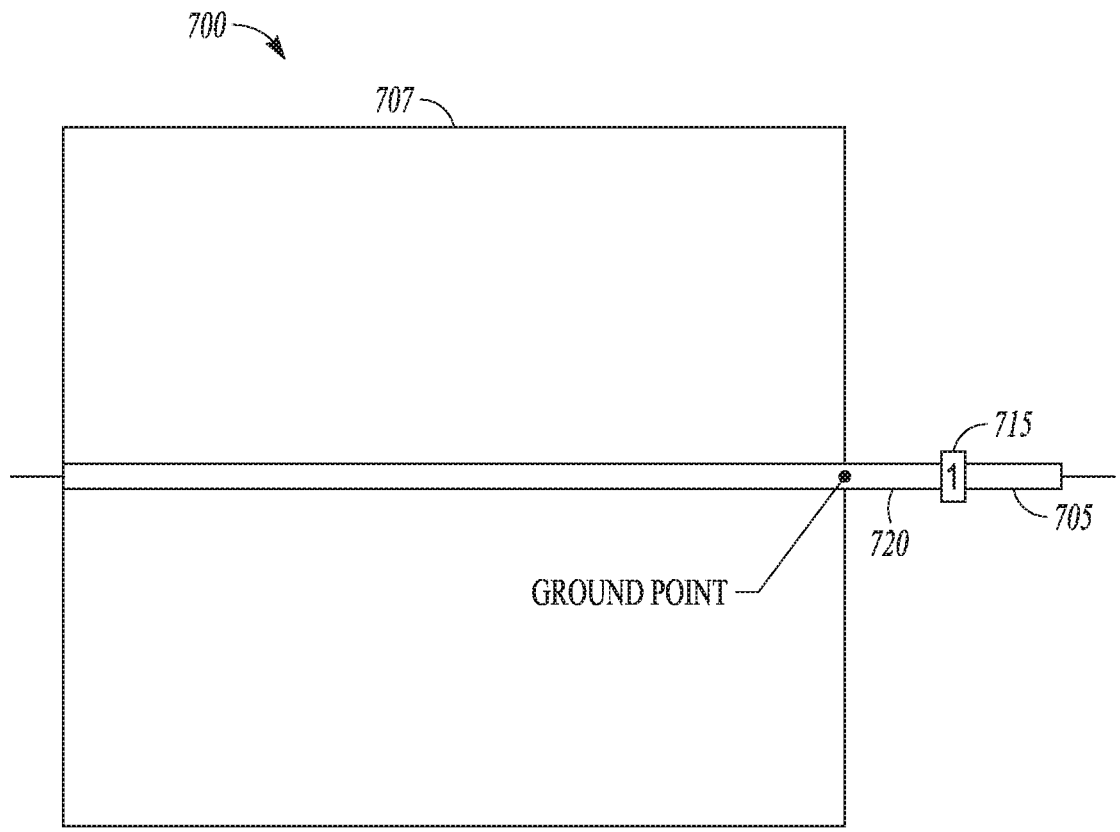
FIG. 7 shows an example of a monopole-like antenna.

According to some examples, the first conductive strip segment 205 and the second conductive strip segment 210 of FIG. 2 comprise monopole-like antennas. FIG. 7 shows an example of a monopole-like antenna. A first conductive strip segment 705 is attached to an antenna feed point 715 (indicated by the "1" in the FIG. 7). Another conductive strip segment 720 connects the feed point to a ground point. A ground plane 707 (e.g., a ground plane of an external medical communicator assembly) shields the rest of the antenna circuit. A dipole antenna consists of two identical conductors with the feed point at the joining point of the two conductors. The antenna 700 of FIG. 7 is monopole-like because it behaves as one arm of a dipole antenna due to the ground plane. Note that the antenna feed point is asymmetrical and is offset from where a dipole joining point would normally be located (e.g., at the ground plane). For the monopole-like antenna of FIG. 7, the direction of the antenna can be easily changed by re-orienting the external device.

Figure 8:
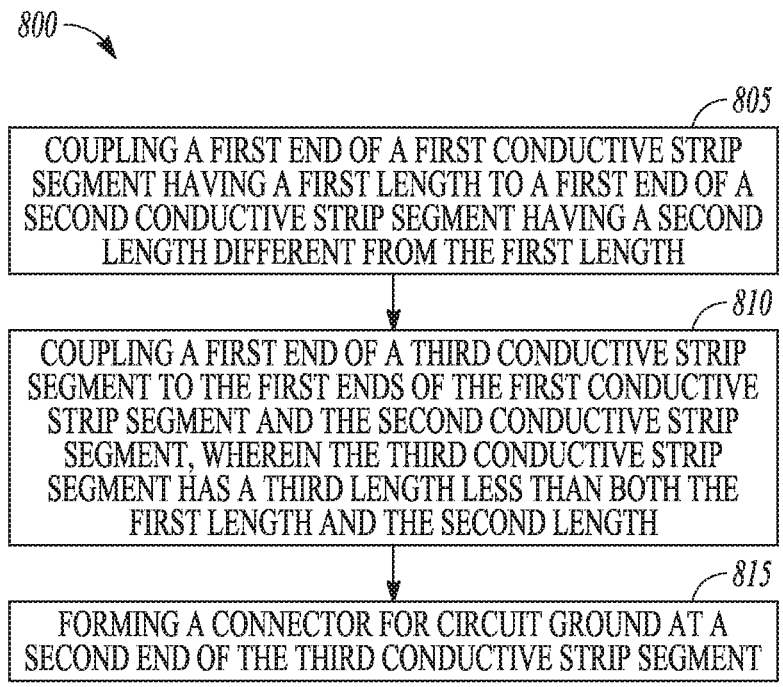
FIG. 8 shows a flow diagram of an example of a method of forming a multi-band diversity antenna.

FIG. 8 shows a flow diagram of an example of a method 800 of forming a multi-band diversity antenna element such as the antenna element example shown in FIG. 2. At 805, a first end of a first conductive strip segment having a first length is coupled to a first end of a second conductive strip segment having a second length different from the first length. The first conductive strip segment may be conductively coupled to the second conductive strip segment such as by soldering, metal trace printing, etc.

At 810, a first end of a third conductive strip segment is coupled to the first ends of the first conductive strip segment and the second conductive strip segment. The third conductive strip segment has a third length that is less than both of the first length and the second length. In certain examples, the third length is a specified fraction of the first length.

The conductive trace segments may be arranged on a flexible circuit substrate such as by printing or by a metal deposition process. The conductive strip segments may be formed with one or more turns. In certain examples, the conductive strip segments are formed so that sections of the first conductive strip segment are parallel to the second conductive strip segment as shown in the example of FIG. 2.

At 815, a connector for circuit ground is formed at a second end of the third conductive strip segment. In certain examples, the ground connector is shielded by a ground plane to form a monopole-like antenna as shown in the example of FIG. 7. The first ends of the first, second, and third conductive strip segments can be coupled (e.g., conductively coupled) to a drive node of a wireless communication circuit (such as at feed point 715 of FIG. 7). The wireless communication circuit can be operated without an antenna impedance matching circuit.

As explained herein, to provide multi-band diversity, the first conductive strip segment can be configured (e. g., by length) to provide a first specified operating frequency range at or near a fundamental resonance mode corresponding to a length equal to the first length plus the third length, and the second conductive strip segment can be configured to provide a second, higher, specified operating frequency range at or near a fundamental resonance mode corresponding to a length equal to the second length plus the third length. In certain examples a bend is formed in the first and second conductive strip segments as described previously to provide polarization diversity.

The method 800 can include forming an antenna system that can communicate using more than two frequency bands. In some examples, the method 800 includes coupling a fourth conductive strip segment to the first end of the third conductive strip segment. The fourth conductive strip segment may have a fourth length that is less than the first length or the second length. The fourth conductive strip segment may be configured to provide a third specified operating frequency range at or near a resonance mode of a higher order than a fundamental resonance mode corresponding to a length equal to the length of the fourth conductive strip segment plus the length of the third conductive strip segment.

The antenna elements described herein simplify the design of external medical communicators by enabling wireless communication with a variety of medical devices using multiple frequency bands, such as the MICS, ISM, SRD, and Wi-Fi bands for example. The antenna elements also provide directional diversity by reducing polarity of the antenna assembly to simplify communication with a medical device in a clinical setting.

Additional Notes and Examples

Example 1 includes subject matter (such as an antenna for electrical coupling to a drive node of a wireless communication circuit of an external medical communicator) including: a first conductive strip segment having a first length; a second conductive strip segment having a second length different from the first length and coupled to the first conductive strip segment at a feed point to be electrically coupled to the drive node; and a third conductive strip segment having a third length less than both the first length and the second length, wherein a first end of the third conductive strip is coupled to the feed point and a second end coupled to circuit ground. The first conductive strip segment is configured to provide a first specified operating frequency range at or near a fundamental resonance mode corresponding to the first length plus the third length, and the second conductive strip segment is configured to provide a second, higher, specified operating frequency range at or near a fundamental resonance mode corresponding to the second length plus the third length.

In Example 2, the subject matter of Example 1 can optionally include the third length of the third conductive strip segment being a specified fraction of an overall length corresponding to the first length plus the third length. The antenna can optionally be coupled to the drive node to transfer information without an impedance matching circuit.

In Example 3, the subject matter of Example 1 or Example 2 optionally includes a first conductive strip segment including a plurality of turns so that a first section of the first conductive strip segment is arranged to be substantially parallel to the second conductive strip segment on a first side and a second section of the first conductive strip segment is arranged to be substantially parallel to the second conductive strip segment on a second side.

In Example 4, the subject matter of Example 3 optionally includes the second conductive strip segment and the first conductive strip segment arranged on a flexible circuit substrate. The flexible circuit substrate, the second conductive strip segment, and the sections of the first conductive strip segment parallel to the second conductive strip segment optionally include a bend of substantially a right angle.

In Example 5, the subject matter of one or any combination of Examples 1-4 optionally includes a first portion of the first conductive strip segment and a first portion of the second conductive strip segment being coplanar in a first plane, and a second portions of the first conductive strip segment and a second portion of the second conductive strip segment being coplanar in a second plane. The second plane can be substantially orthogonal to the first plane.

In example 6, the subject matter of one or any combination of Examples 1-5 optionally includes the first conductive strip segment and the third conductive strip segment sized for communication in a medical implant communication service (MICS) extended frequency band, and the second conductive strip segment and the third conductive strip segment sized for communication in a short range device (SRD) or a North American industrial, scientific, and medical (ISM) frequency band.

In Example 7, the subject matter of one or any combination of Examples 1-6 optionally includes a fourth conductive strip segment for electrical coupling to a second drive node of the wireless communication circuit. The fourth conductive strip segment optionally has a fourth length less than the first length or the second length and is coupled to the third conductive strip segment at a second feed point to the second drive node. The fourth conductive strip segment can be configured to provide a third specified operating frequency range at or near a resonance mode of a higher order than a fundamental resonance mode corresponding to the fourth length plus the third length.

In Example 8, the subject matter of Example 7 optionally includes the fourth conductive strip segment and the third conductive strip segment sized for communication in a Wi-Fi frequency band. In another example, the subject matter of Example 7 optionally includes the fourth conductive strip segment and the third conductive strip segment sized for communication using Bluetooth wireless communication standards. The term "Bluetooth" is used herein to indicate that a component is capable of communicating according to a standard for wireless exchange of data over short distances using short-wavelength UHF radio waves in the ISM band from 2.4-2.485 Gigahertz. Standards for Bluetooth communication are managed by the Bluetooth Special Interest Group.

In Example 9, the subject matter of one or any combination of Examples 1-8 optionally includes the first conductive strip segment and the second conductive strip segment comprising monopole-like antennas.

Example 10 can include subject matter (such as a method of making or forming a multi-band diversity antenna element for an external medical communicator, means for performing acts, or a machine readable medium that can cause the machine to perform acts) including coupling a first end of a first conductive strip segment having a first length to a first end of a second conductive strip segment having a second length different from the first length; coupling a first end of a third conductive strip segment to the first ends of the first conductive strip segment and the second conductive strip segment, wherein the third conductive strip segment has a third length less than both the first length and the second length and is a specified fraction of the first length; and forming a connector for circuit ground at a second end of the third conductive strip segment. The first conductive strip segment can be configured to provide a first specified operating frequency range at or near a fundamental resonance mode corresponding to the first length plus the third length, and the second conductive strip segment can be configured to provide a second, higher, specified operating frequency range at or near a fundamental resonance mode corresponding to the second length plus the third length.

In Example 11, the subject matter of Example 10 optionally includes forming a plurality of turns in the first conductive strip segment to arrange a first section of the first conductive strip segment to be substantially parallel to the second conductive strip segment on a first side and arrange a second section of the first conductive strip segment to be substantially parallel to the second conductive strip segment on a second side.

In Example 12, the subject matter of Example 11 optionally includes forming a bend of substantially ninety degrees in the second conductive strip segment and the first and second sections of the first conductive strip segment parallel to the second conductive strip segment, wherein a first portion of the second conductive strip segment is coplanar in a first plane with first portions of the first and second sections of the first conductive strip segment, and a second portion of the second conductive is coplanar in a second plane with second portions of the first and second sections of the first conductive strip segment.

In Example 13, the subject matter of Example 11 or Example 12 optionally includes arranging the first conductive strip segment and the second conductive strip segment on a flexible circuit substrate. The forming the plurality of turns in the first conductive strip segment optionally includes forming the first and second sections of the first conductive strip segment to be coplanar with the second conductive strip segment on the flexible circuit substrate. The subject matter of Example 11 or Example 12 may also optionally include forming a bend of substantially a right angle in the flexible circuit substrate, the second conductive strip segment, and the first and second sections of the first conductive strip segment.

In Example 14, the subject matter of one or any combination of Examples 10-13 optionally includes coupling a fourth conductive strip segment to the first end of the third conductive strip segment, wherein the fourth conductive strip segment has a fourth length less than the first length or the second length is configured to provide a third specified operating frequency range at or near a resonance mode of a higher order than a fundamental resonance mode corresponding to the fourth length plus the third length.

In Example 15, the subject matter of one or any combination of Examples 10-14 optionally includes coupling the second end of the third conductive strip segment to a ground plane of the external medical communicator; and electrically shielding a connection to the antenna with the ground plane to form a monopole-like antenna.

In Example 16, the subject matter of one or any combination of Example 10-15 optionally includes coupling the first ends of the first, second, and third conductive strip segments to a drive node of a wireless communication circuit of the external medical communicator and operating the wireless communication circuit without an antenna impedance matching circuit.

Example 17 can include subject matter, or can optionally be combined with one or a combination of Examples 1-16 to include subject matter (such as an electronic assembly for an external medical device), including a wireless transceiver; and an antenna coupled to a drive node of the wireless transceiver. The antenna optionally includes: a first conductive strip segment having a first length; a second conductive strip segment having a second length different from the first length and coupled to the first conductive strip segment at a feed point to be electrically coupled to the drive node; and a third conductive strip segment having a third length less than both the first length and the second length, wherein a first end of the third conductive strip segment is coupled to the feed point and a second end coupled to circuit ground. The first conductive strip segment is optionally configured to provide a first specified operating frequency range at or near a fundamental resonance mode corresponding to the first length plus the third length, and the second conductive strip segment is configured to provide a second, higher, specified operating frequency range at or near a fundamental resonance mode corresponding to the second length plus the third length.

In Example 18, the subject matter of Example 17 optionally includes the first conductive strip segment including a plurality of turns so that a first section of the first conductive strip segment is arranged to be substantially parallel to the second conductive strip segment on a first side and a second section of the first conductive strip segment is arranged to be substantially parallel to the second conductive strip segment on a second side.

In Example 19, the subject matter of claim 18 optionally includes the second conductive strip segment and the sections of the first conductive strip segment parallel to the second conductive strip segment including a bend of substantially ninety degrees.

In Example 20, the subject matter of one or any combination of Examples 17-19 optionally includes a fourth conductive strip segment for electrical coupling to a second drive node of the wireless communication circuit. The fourth conductive strip segment has a fourth length less than the first length or the second length and is coupled to the third conductive strip segment at a second feed point to the second drive node. The fourth conductive strip segment is optionally configured to provide a third specified operating frequency range at or near a resonance mode of a higher order than a fundamental resonance mode corresponding to the fourth length plus the third length.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An external medical device communicator configured to communicate wireless signals to a medical device, the external medical device communicator comprising:
   a wireless communication circuit comprising a drive node;
   a multi-band diversity antenna element having a monopole structure, the multi-band diversity antenna element comprising:
      a first conductive strip segment having a first length;
      a second conductive strip segment having a second length different from the first length and coupled to the first conductive strip segment at a feed point to be electrically coupled to the drive node;
      a third conductive strip segment having a third length less than both the first length and the second length, wherein a first end of the third conductive strip segment is coupled to the feed point and a second end is coupled to a circuit ground; and
   wherein the first conductive strip segment and the third conductive strip segments are sized for communication with the medical device in a first frequency band and the second conductive strip segment and the third conductive strip segment are sized for communication with the medical device in a second frequency band, wherein the second frequency band comprises a higher range of frequencies than the first frequency band.

2. The external medical device communicator of claim 1, wherein the third length is a specified fraction of an overall length corresponding to the first length plus the third length, and the antenna is coupled to the drive node to transfer information without an impedance matching circuit.

3. The external medical device communicator of claim 1, wherein the first conductive strip segment includes a plurality of turns so that a first section of the first conductive strip segment is arranged to be parallel to the second conductive strip segment on a first side and a second section of the first conductive strip segment is arranged to be parallel to the second conductive strip segment on a second side.

4. The external medical device communicator of claim 3, wherein the second conductive strip segment and the first conductive strip segment are arranged on a flexible circuit substrate, wherein the flexible circuit substrate, the second conductive strip segment, and the sections of the first conductive strip segment parallel to the second conductive strip segment include a bend of a right angle.

5. The external medical device communicator of claim 3, wherein a first portion of the first conductive strip segment and a first portion of the second conductive strip segment are coplanar in a first plane, and a second portions of the first conductive strip segment and a second portion of the second conductive strip segment are coplanar in a second plane, wherein the second plane is orthogonal to the first plane.

6. The external medical device communicator of claim 1, wherein the first frequency band is a medical implant communication service (MICS) extended frequency band, and the second frequency band is a short range device (SRD) or a North American industrial, scientific, and medical (ISM) frequency band.

7. The external medical device communicator of claim 1, including a fourth conductive strip segment for electrical coupling to a second drive node of the wireless communication circuit, wherein the fourth conductive strip segment has a fourth length less than the first length or the second length and is coupled to the third conductive strip segment at a second feed point to the second drive node, and wherein the fourth conductive strip segment is configured to provide a third specified operating frequency range at or near a resonance mode of a higher order than a fundamental resonance mode corresponding to the fourth length plus the third length.

8. The external medical device communicator of claim 7, wherein the fourth conductive strip segment and the third conductive strip segment are sized for communication in a Wi-Fi frequency band.

9. The external medical device communicator of claim 1, wherein the second conductive strip segment and the first conductive strip segment are arranged on a flexible circuit substrate, wherein the flexible circuit substrate, the second conductive strip segment, and the first conductive strip segment include a bend of a right angle.

10. A method of forming a multi-band diversity antenna element for an external medical communicator, wherein the external medical communicator comprises a wireless communication circuit comprising a drive node, and wherein the multi-band diversity antenna element comprises a first conductive strip segment, a second conductive strip segment, and a third conductive strip segment, and wherein the multi-band diversity antenna element has a monopole structure, the method comprising:
   coupling a first end of the first conductive strip segment having a first length to a first end of the second conductive strip segment having a second length different from the first length;
   coupling a first end of the third conductive strip segment to the first ends of the first conductive strip segment and the second conductive strip segment, wherein the third conductive strip segment has a third length less than both the first length and the second length and is a specified fraction of the first length;
   coupling the multi-band diversity antenna element to the drive node; and
   forming a connector for circuit ground at a second end of the third conductive strip segment, wherein the first conductive strip segment and the third conductive strip segments are sized for communication with a medical device in a first frequency band and the second conductive strip segment and the third conductive strip segment are sized for communication with the medical device in a second frequency band, wherein the second frequency band comprises a higher range of frequencies than the first frequency band.

11. The method of claim 10, including forming a plurality of turns in the first conductive strip segment to arrange a first section of the first conductive strip segment to be parallel to the second conductive strip segment on a first side and arrange a second section of the first conductive strip segment to be parallel to the second conductive strip segment on a second side.

12. The method of claim 11, including forming a bend of a right angle in the second conductive strip segment and the first and second sections of the first conductive strip segment parallel to the second conductive strip segment, wherein a first portion of the second conductive strip segment is coplanar in a first plane with first portions of the first and second sections of the first conductive strip segment, and a second portion of the second conductive is coplanar in a second plane with second portions of the first and second sections of the first conductive strip segment.

13. The method of claim 11, including: arranging the first conductive strip segment and the second conductive strip segment on a flexible circuit substrate, wherein forming the plurality of turns in the first conductive strip segment includes forming the first and second sections of the first conductive strip segment to be coplanar with the second conductive strip segment on the flexible circuit substrate; and forming a bend of a right angle in the flexible circuit substrate, the second conductive strip segment, and the first and second sections of the first conductive strip segment.

14. The method of claim 11, including: arranging the first conductive strip segment and the second conductive strip segment on a flexible circuit substrate, and forming a bend of a right angle in the flexible circuit substrate, the second conductive strip segment, and the first and second sections of the first conductive strip segment.

15. The method of claim 10, including coupling a fourth conductive strip segment to the first end of the third conductive strip segment, wherein the fourth conductive strip segment has a fourth length less than the first length or the second length and is configured to provide a third specified operating frequency range at or near a resonance mode of a higher order than a fundamental resonance mode corresponding to the fourth length plus the third length.

16. The method of claim 10, including: coupling the second end of the third conductive strip segment to a ground plane of the external medical communicator; and electrically shielding a connection to the antenna with the ground plane to form a monopole antenna.

17. The method of claim 10, including coupling the first ends of the first, second, and third conductive strip segments to a drive node of a wireless communication circuit of the external medical communicator and operating the wireless communication circuit without an antenna impedance matching circuit.

18. A medical communication system comprising:
a medical device;
an external medical device communicator configured to communicate wireless signals to the medical device, the external medical device communicator comprising:
a wireless communication circuit comprising a drive node;
a multi-band diversity antenna element having a monopole structure, the multi-band diversity antenna element comprising:
a first conductive strip segment having a first length;
a second conductive strip segment having a second length different from the first length and coupled to the first conductive strip segment at a feed point to be electrically coupled to the drive node;
a third conductive strip segment having a third length less than both the first length and the second length, wherein a first end of the third conductive strip segment is coupled to the feed point and a second end is coupled to a circuit ground; and
wherein the first conductive strip segment and the third conductive strip segment are sized for communication with the medical device in a first frequency band and the second conductive strip segment and the third conductive strip segment are sized for communication with the medical device in a second frequency band, wherein the second frequency band comprises a higher range of frequencies than the first frequency band.

19. The medical communication system of claim 18, wherein the medical device is an implantable medical device.

20. The medical communication system of claim 19, wherein the medical device is one of a cardiac function management (CFM) device, an implantable diagnostic device, an implantable drug delivery system, and an implantable device having neural stimulation capability.

* * * * *